United States Patent

Hamada et al.

Patent Number: 5,214,202
Date of Patent: May 25, 1993

[54] METHOD FOR PREPARING BENZOIC ACID DERIVATIVES

[75] Inventors: Yoshinori Hamada, Hyogo; Isamu Yamada, Osaka; Masaaki Uenaka, Osaka; Teruo Sakata, Osaka, all of Japan

[73] Assignee: Shionogi & Co., Ltd., Osaka, Japan

[21] Appl. No.: 778,985

[22] PCT Filed: Mar. 15, 1991

[86] PCT No.: PCT/JP91/00350
§ 371 Date: Nov. 6, 1991
§ 102(e) Date: Nov. 6, 1991

[87] PCT Pub. No.: WO91/14673
PCT Pub. Date: Oct. 3, 1991

[30] Foreign Application Priority Data
Mar. 20, 1990 [JP] Japan ................. 2-71433

[51] Int. Cl.$^5$ ............................................. C07C 101/60
[52] U.S. Cl. ................................. 562/457; 564/183; 564/189; 564/221
[58] Field of Search ............. 562/457; 564/183, 189, 564/221

[56] References Cited

U.S. PATENT DOCUMENTS

| | | | |
|---|---|---|---|
| 4,221,814 | 9/1980 | Takaku et al. | 562/457 X |
| 4,221,815 | 9/1980 | Weyer et al. | 562/457 X |
| 4,227,014 | 10/1980 | Shepherd | 562/457 |
| 4,989,090 | 12/1989 | De Vries et al. | 562/457 X |

Primary Examiner—Paul F. Shaver
Attorney, Agent, or Firm—Wenderoth, Lind & Ponack

[57] ABSTRACT

This invention relates to a synthesis method favorable for the industrial production of a benzoic acid derivative having a retinoid activity of the general formula:

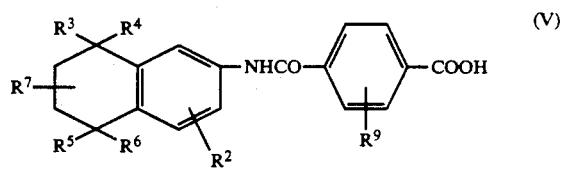

wherein the derivative can be obtained by a simple procedure in safety with high yield.

Specifically, this invention relates to a synthesis method characterized in that only one vessel is needed for several reactions in the different steps of subjecting acetanilide as a starting material, which is readily available and safe to handle, to Friedel-Crafts reaction with 2,5-dimethyl-2,5-dichlorohexane; subjecting the thus obtained compound to acyl exchange reaction with monomethyl ester terephthalic chloride, followed by hydrolysis; and recrystallizing from a mixture of methanol and water.

Moreover, the crystals in novel form obtained by the synthesis method of this invention are suitable for formulation, because the amount of solvents remaining therein after recrystallization is small and the grain size thereof is uniform.

4 Claims, 5 Drawing Sheets

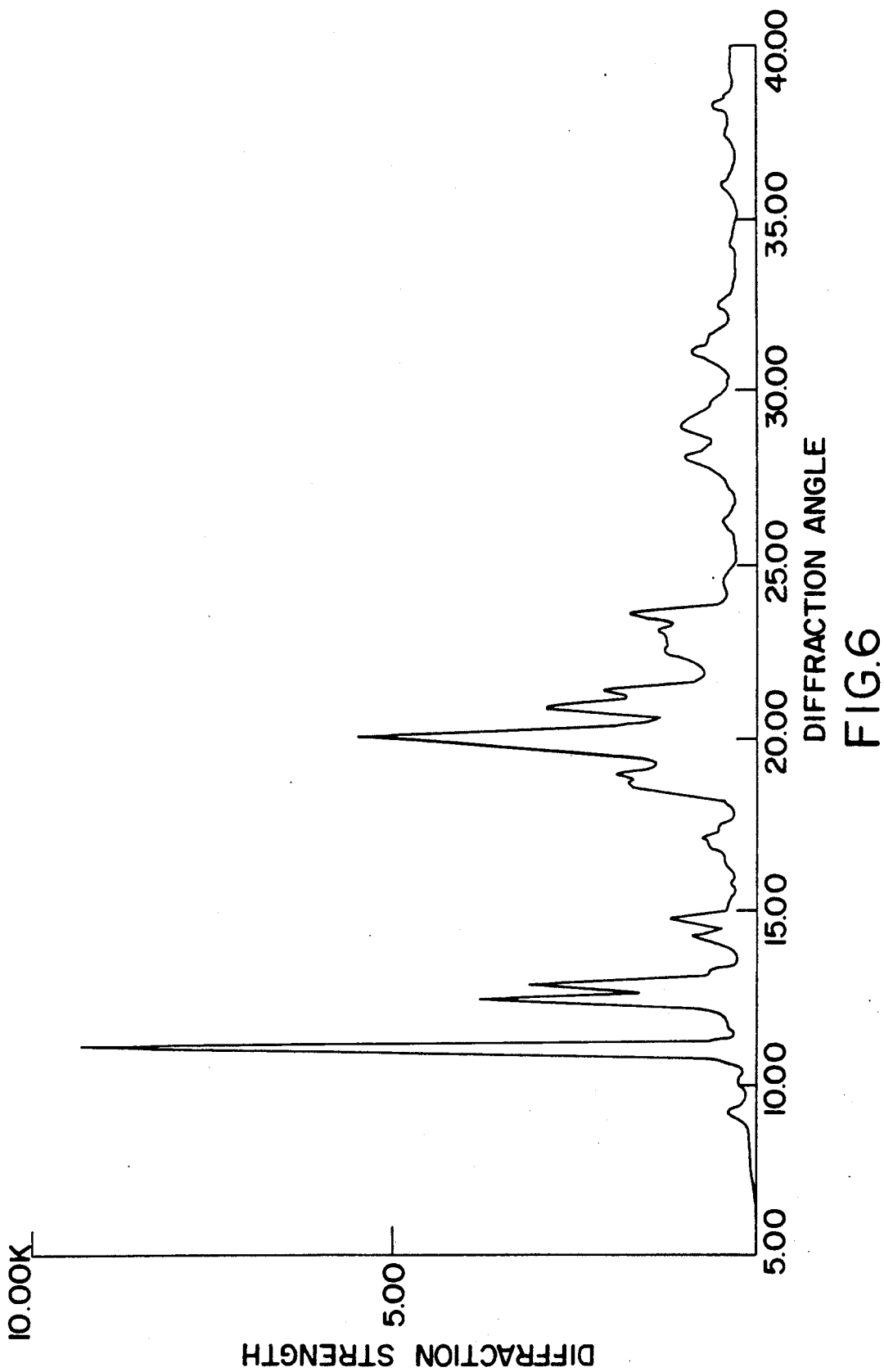

METHOD FOR PREPARING BENZOIC ACID DERIVATIVES

FIELD OF THE INVENTION

This invention relates to a method for preparing a compound having a retinoid activity, which is favorable for the production of such a compound on an industrial scale. It also relates to a novel crystal form of 4-[(5,6,7,8-tetrahydro-5,5,8,8-tetramethyl-2-naphthyl)carbamoyl] benzoic acid which is useful as a medicament, and a method for preparation thereof.

BACKGROUND OF THE INVENTION

The compound obtained by this invention has been prepared by allowing tetrahydronaphthylamine derivative to react with monoester terephthalic halide and then subjecting to de-esterification (JP. Unexamd Pat. Publn. No. 61-76440). This method is, however, unfavorable for the production of the objective compound on an industrial scale, because starting amine derivative is not readily available, this amine derivative is toxic to the human body and more complicated steps are required. Moreover, it may be difficult in some cases to say that the obtained compound by this method is suitable for formulation.

DISCLOSURE OF THE INVENTION

This invention provides a method for preparing the objective compound advantageously in a simple procedure, with high purity and yield from a starting material which is readily available on an industrial scale, inexpensive, and not harmful to the human body.

The present invention provides a process for the preparation of the objective compound (V):

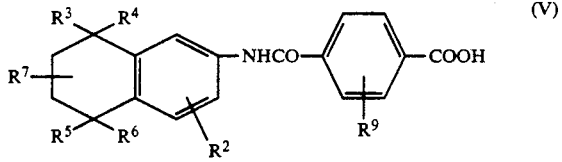

wherein $R^2$, $R^7$ and $R^9$ are independently hydrogen or lower alkyl, and $R^3$, $R^4$, $R^5$ and $R^6$ are independently lower alkyl, which comprises:

(a) subjecting acyl aniline derivative (I):

wherein $R^1$ is lower alkyl or aryl and $R^2$ is the same as above, and 1,4-butyl dihalide derivative (II):

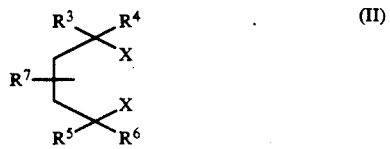

wherein $R^3$, $R^4$, $R^5$, $R^6$ and $R^7$ are respectively the same as above, and X is halogen, to Friedel-Crafts reaction in an inert solvent in the presence of a Friedel-Crafts catalyst, thereby obtaining a novel bicyclic amide compound of the general formula (III):

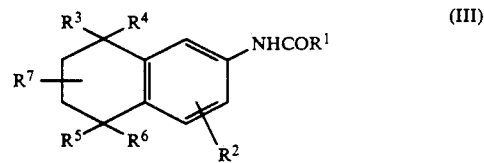

wherein $R^1$, $R^2$, $R^3$, $R^4$, $R^5$, $R^6$ and $R^7$ are respectively the same as above;

(b) reacting the thus obtained bicyclic amide compound with a halogenating agent and an alcohol in sequence, and then subjecting to acyl exchange reaction with monoester terephthalic halide, thereby obtaining an amide compound of the general formula (IV):

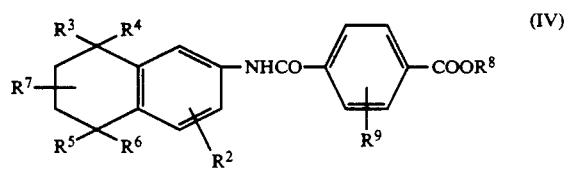

wherein $R^2$, $R^3$, $R^4$, $R^5$, $R^6$, $R^7$ and $R^9$ are respectively the same as above, and $R^8$ is lower alkyl; and (c) hydrolizing this compound.

In this invention, the term "lower alkyl" refers to an alkyl group of 1 to 4 carbon atoms, examples of which are methyl, ethyl, i-propyl, butyl, i-butyl, t-butyl and the like.

The term "aryl" refers to a phenyl group, a substituted phenyl group or the like. The substituent replacing the hydrogen of a phenyl ring can be any one of those which are inactive to the reaction, examples of which are lower alkyl, lower alkoxy carbonyl, nitro, halogen and the like.

As the Friedel-Crafts catalyst used in the step (a), conventional catalysts for Friedel-Crafts reaction can be used, such as Lewis acids (e.g., $AlCl_3$, $AlBr_3$, $ZnCl_2$, $ZnCl_4$, $ZnBr_2$, $ZnBr_4$, $BF_3$ and a solvation thereof with an ether, $SnCl_4$, $SnBr_4$, $TiCl_4$ and $TiBr_4$), protoic acids (e.g., sulfuric acid, anhydrous hydrofluoric acid, phosphoric acid, polyphosphoric acid, perchloric acid, chlorosulfonic acid, fluorosulfonic acid, organic sulfonic acids, trifluoroacetic acid, chloroacetic acid, and the like), and cation-exchange resins, metal-cation forming agent (e.g., $AgClO_4$, $AgBF_4$, $AgPO_4$, $AgSbF_6$, $AgPF_6$, and $AgAsF_6$). Particularly preferred are Lewis acids. The molar amount of catalysts to be used is 0.5- to 5-times, preferably 1- to 3-times, and more preferably 1.5- to 2-times the molar amount of acylated aniline to be used as a starting material.

Although acylated aniline may be used in a molar amount equivalent to that of butyl dihalide, preferable results can be obtained when one of two compounds is used in an excess amount to the other. For example, butyl dihalide is preferably used in an amount of 0.5 to 3 moles and more preferably 1.5 to 2 moles per 1 mole of acylated aniline.

As the solvent, carbon disulfide, ethers, halogenated hydrocarbons, nitro alkanes or the like can be used, with halogenated hydrocarbons being particularly desirable.

The reaction can be conducted at room temperature, or under heating or cooling condition at a temperature from −70° C. to 50° C. Preferred is the reaction at room temperature or under cooling conditions.

Sufficient time for the reaction, although it depends upon the reaction temperature, is in the range of 0.5 to 20 hours.

Examples of the halogenating agent used in the step (b) include phosphorus trihalides, phosphorus oxyhalides, phosphorus pentahalides, thionyl halides and like. Particularly preferred is phosphorus pentachloride. As the alcohol, lower alkanols are preferred and methanol is favorable for use in the production on an industrial scale.

As the reaction temperature, room temperature is employed or the reaction is conducted under cooling condition. Preferred is the reaction under cooling condition.

The hydrolysis in the step (c) can be conducted under basic condition at room temperature, or heating conditions. When heating, the reaction can rapidly proceed.

In other words, 4-[(5,6,7,8-tetrahydro-5,5,8,8-tetramethyl-2-naphthyl)carbomoyl]benzoic acid which is one embodiment of this invention can be obtained by the steps of:

(a) subjecting the acylated aniline derivative (I):

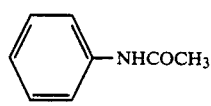

and the 1,4-butyl dihalide derivative (II):

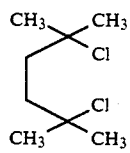

to Friedel-Crafts reaction, to give the bicyclic amide compound of the formula (III):

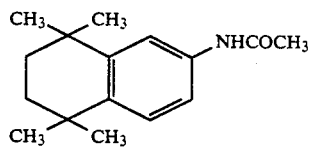

(b) reacting the compound obtained in the step (a) with monoester terephthalic halide to form the compound of the formula (IV):

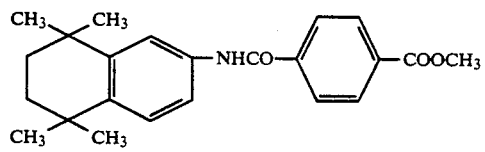

(c) subjecting the compound (IV) obtained in the step (b) to de-esterification.

According to the method described in the aforementioned prior art reference, JP. Unexamd. Pat. Publn. No. 61-76440, 5,6,7,8-tetrahydro-5,5,8,8-tetramethyl-2-naphthylamine as a starting material is reacted with monomethyl terephthalic chloride to form the methyl ester of the objective compound, which is then dissolved in a mixture of methanol and water, and the resultant solution is subjected to hydrolysis by the addition of an aqueous solution of sodium hydroxide. Thereafter, crystals obtained by extraction are recrystallized from a mixture of ethyl acetate and hexane to give the objective compound.

On the other hand, according to the synthesis method of this invention, hydrochloric acid is added just after the hydrolysis, and precipitated crystals are recrystallized from a methanol type solvent to yield the objective compound. For this reason, a complicated procedure such as extraction and removal by evaporation required in the prior art method can be omitted and it is therefore possible to successively perform several different steps in the same reaction vessel. Moreover, the procedure is simple because the solvent for recrystallization is the same solvent type as that used in the reaction.

In this invention, the term "methanol type solvent" refers to methanol or a mixed solvent of methanol and water, which is preferably used. The amount of water to be used is preferably 0.5- to 2-times the amount of methanol, and it is most preferable that water is used in the same amount as that of methanol.

The compound of this invention has an extremely high physiological activity, and handling in a closed system is therefore particularly required. From this point of view, the method of this invention can be said to be advantageous in that its procedure is simple, and can be carried out in the same vessel.

It is difficult to obtain 5,6,7,8-tetrahydro-5,5,8,8-tetramethyl-2-naphthylamine in great quantities at a low price, which amine has been used as a starting material in the prior art method, and generally many amines are hemotoxic.

In contrast to this, acetanilide used as a starting material in the method of this invention is available in great quantities and is safe to handle.

The data of the X-ray diffraction patterns (FIGS. 5 and 6) of 4-[(5,6,7,8-tetrahydro-5,5,8,8-tetramethyl-2-naphthyl)carbamoyl]benzoic acid crystals obtained in Example 3 described below as an embodiment of the method of this invention and obtained by the prior art method are shown in Tables 1 and 2, respectively.

TABLE 1

| Peak No. | 2 θ | Intensity ratio | Peak No. | 2 θ | Intensity ratio |
|---|---|---|---|---|---|
| 1 | 6.58 | 2685 | 18 | 23.94 | 677 |
| 2 | 7.84 | 455 | 19 | 26.14 | 335 |
| 3 | 9.80 | 177 | 20 | 26.84 | 248 |
| 4 | 11.90 | 664 | 21 | 26.96 | 310 |
| 5 | 13.24 | 10000 | 22 | 27.16 | 469 |
| 6 | 15.74 | 1558 | 23 | 27.8 | 448 |
| 7 | 16.02 | 1671 | 24 | 28.34 | 332 |
| 8 | 16.80 | 871 | 25 | 28.76 | 1552 |
| 9 | 17.52 | 213 | 26 | 29.18 | 202 |
| 10 | 17.76 | 1069 | 27 | 30.2 | 192 |
| 11 | 18.1 | 4112 | 28 | 31.66 | 429 |
| 12 | 19.5 | 2685 | 29 | 31.82 | 213 |
| 13 | 19.86 | 924 | 30 | 33.96 | 166 |
| 14 | 20.56 | 256 | 31 | 35.56 | 227 |
| 15 | 21.54 | 1385 | 32 | 35.78 | 158 |
| 16 | 22.08 | 1326 | 33 | 38.04 | 237 |
| 17 | 22.48 | 987 | 34 | 38.28 | 771 |

TABLE 2

| Peak No. | 2 θ | Intensity ratio | Peak No. | 2 θ | Intensity ratio |
| --- | --- | --- | --- | --- | --- |
| 1 | 11.16 | 10000 | 19 | 23.2 | 599 |
| 2 | 12.56 | 3560 | 20 | 23.62 | 1187 |
| 3 | 12.98 | 2908 | 21 | 26.32 | 216 |
| 4 | 13.34 | 254 | 22 | 28.08 | 489 |
| 5 | 14.3 | 577 | 23 | 28.74 | 289 |
| 6 | 14.84 | 901 | 24 | 28.94 | 515 |
| 7 | 16.92 | 325 | 25 | 29.12 | 392 |
| 8 | 17.12 | 476 | 26 | 29.30 | 252 |
| 9 | 17.46 | 212 | 27 | 30.78 | 158 |
| 10 | 18.62 | 886 | 28 | 30.98 | 424 |
| 11 | 19.02 | 754 | 29 | 31.48 | 230 |
| 12 | 19.52 | 348 | 30 | 31.60 | 175 |
| 13 | 19.72 | 1440 | 31 | 31.66 | 152 |
| 14 | 20.08 | 4151 | 32 | 32.5 | 189 |
| 15 | 20.94 | 1632 | 33 | 36.04 | 240 |
| 16 | 21.42 | 1067 | 34 | 37.82 | 301 |
| 17 | 22.56 | 432 | | | |
| 18 | 22.86 | 381 | | | |

From the results described above, it is found that the crystals synthesized by the respective methods have different crystal forms. When the properties of these crystals are compared with each other, it is found that the amount of methanol remaining in the crystals of the objective compound according to this invention, which has been used as a solvent for recrystallization, is 50 ppm or less, whereas the amounts of ethyl acetate and hexane remaining in the crystals of the objective compound according to the prior art, which have been used as solvents for recrystallization, are 1200 ppm and 190 ppm, respectively. The latter two values are far beyond the provision established by the Welfare Ministry in Japan that the amount of solvents remaining in end products should not be more than the standard value of 50 ppm. From the viewpoint that the aforementioned compound is also used as a medicament, it is difficult to say that this situation is favorable.

Moreover, when the grain sizes of the respective crystals are compared with each other, it is found that the crystals according to the method of this invention have uniform grain size of 0.2 mm or less, whereas the crystals according to the prior art have an ununiform grain size of 1 mm of more. For this reason, according to the method of this invention, there is no need to employ any pulverization step in the formulation, which is extremely advantageous.

As described above, the method of this invention is an excellent one for industrial use, by which the objective compound can be advantageously synthesized by a simple procedure in safety with high yield.

Figure 1:
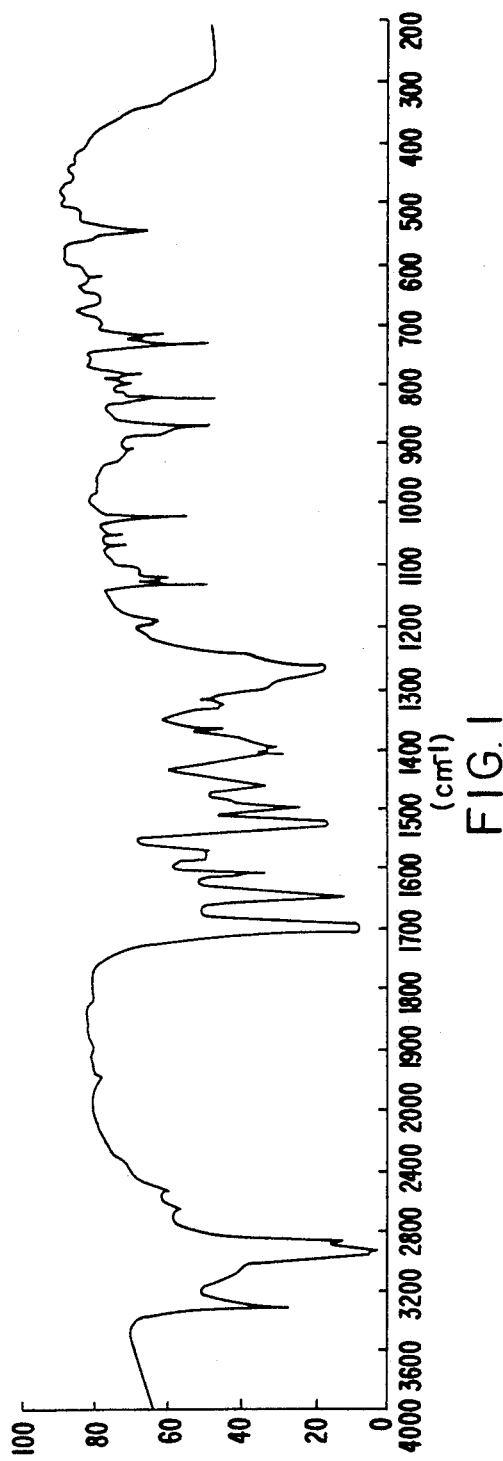
FIG. 1 is a diagram showing the IR spectrum of 4-[(5,6,7,8-tetrahydro-5,5,8,8-tetramethyl-2-naphthyl)-carbamoyl]benzoic acid which is the objective compound synthesized according to the method of this invention. This IR spectrum was obtained by use of Nujol.
Figure 2:
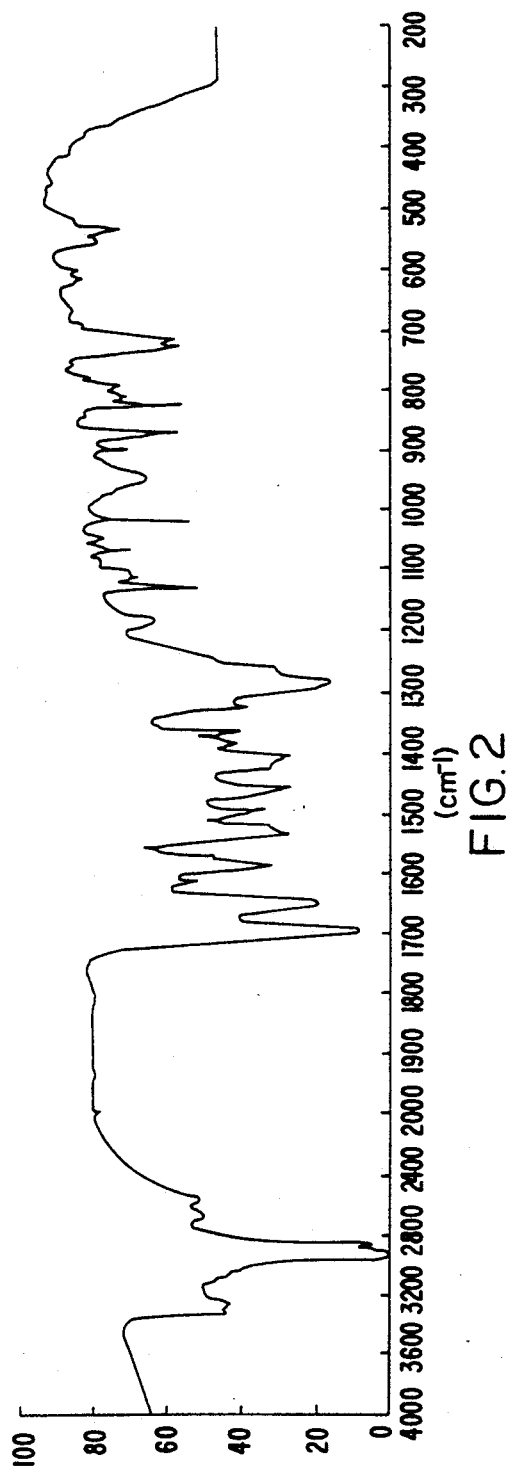
FIG. 2 is a diagram showing the IR spectrum of 4-[(5,6,7,8-tetrahydro-5,5,8,8-tetramethyl-2-naphthyl)-carbamoyl]benzoic acid which was synthesized according to the prior art method. This IR spectrum was obtained by use of Nujol.
Figure 3:
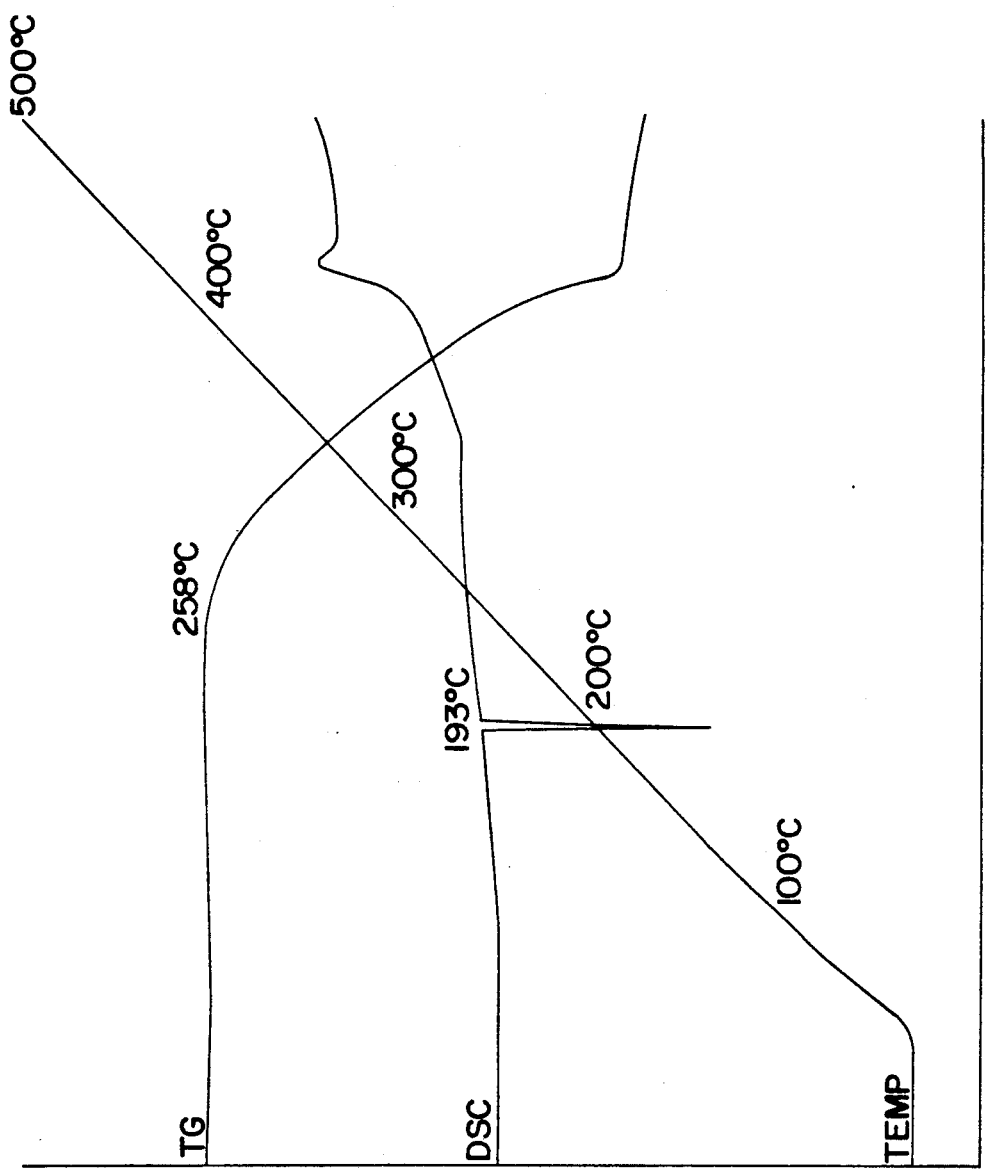
FIG. 3 is a diagram showing the thermal decomposition of the objective compound synthesized according to the production method of this invention. This compound melts at 193° C.
Figure 4:
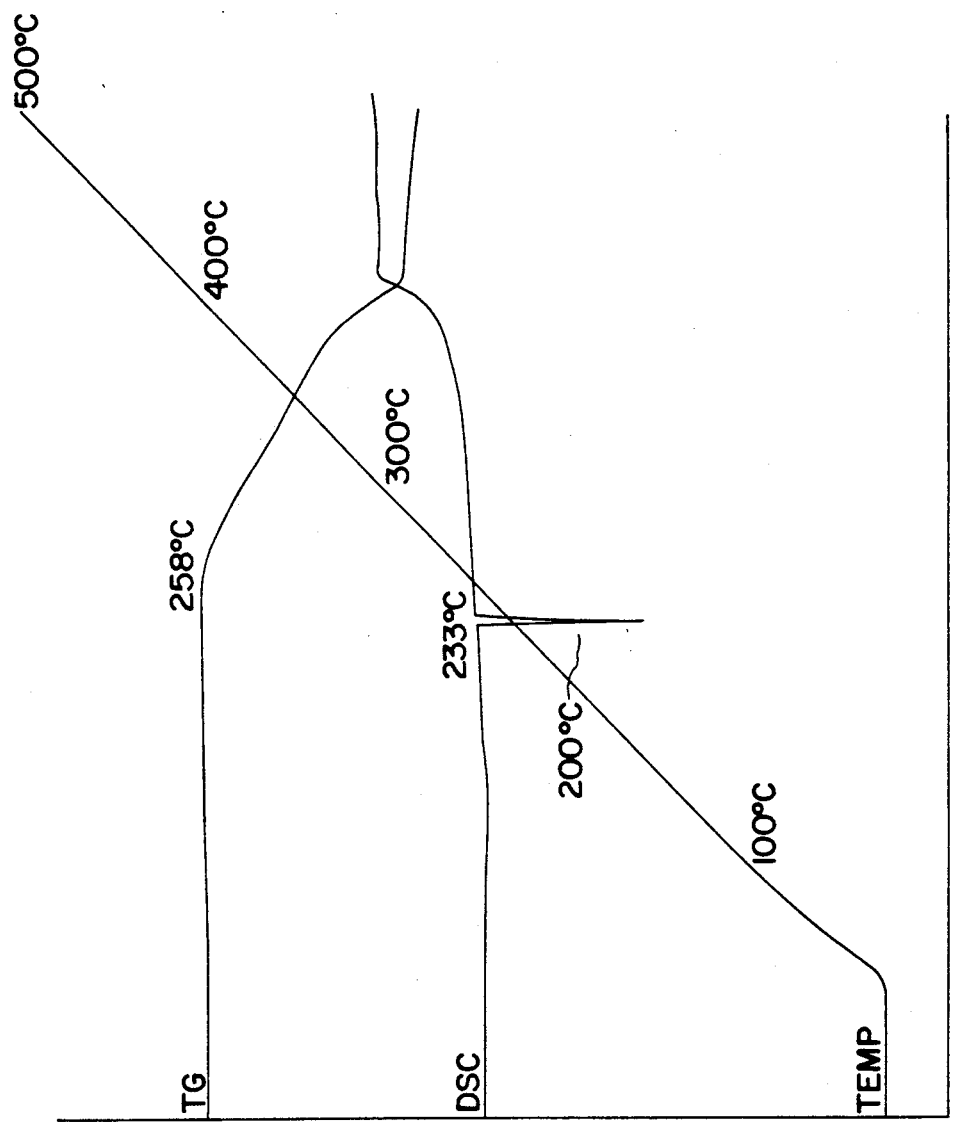
FIG. 4 is a diagram showing the thermal decomposition of the objective compound synthesized according to the prior art method. This compound melts at 233° C.

As can be seen from FIGS. 3 and 4, the objective compound synthesized by the method of this invention has different properties from those of the compound synthesized by the method of the prior art.

Figure 5:
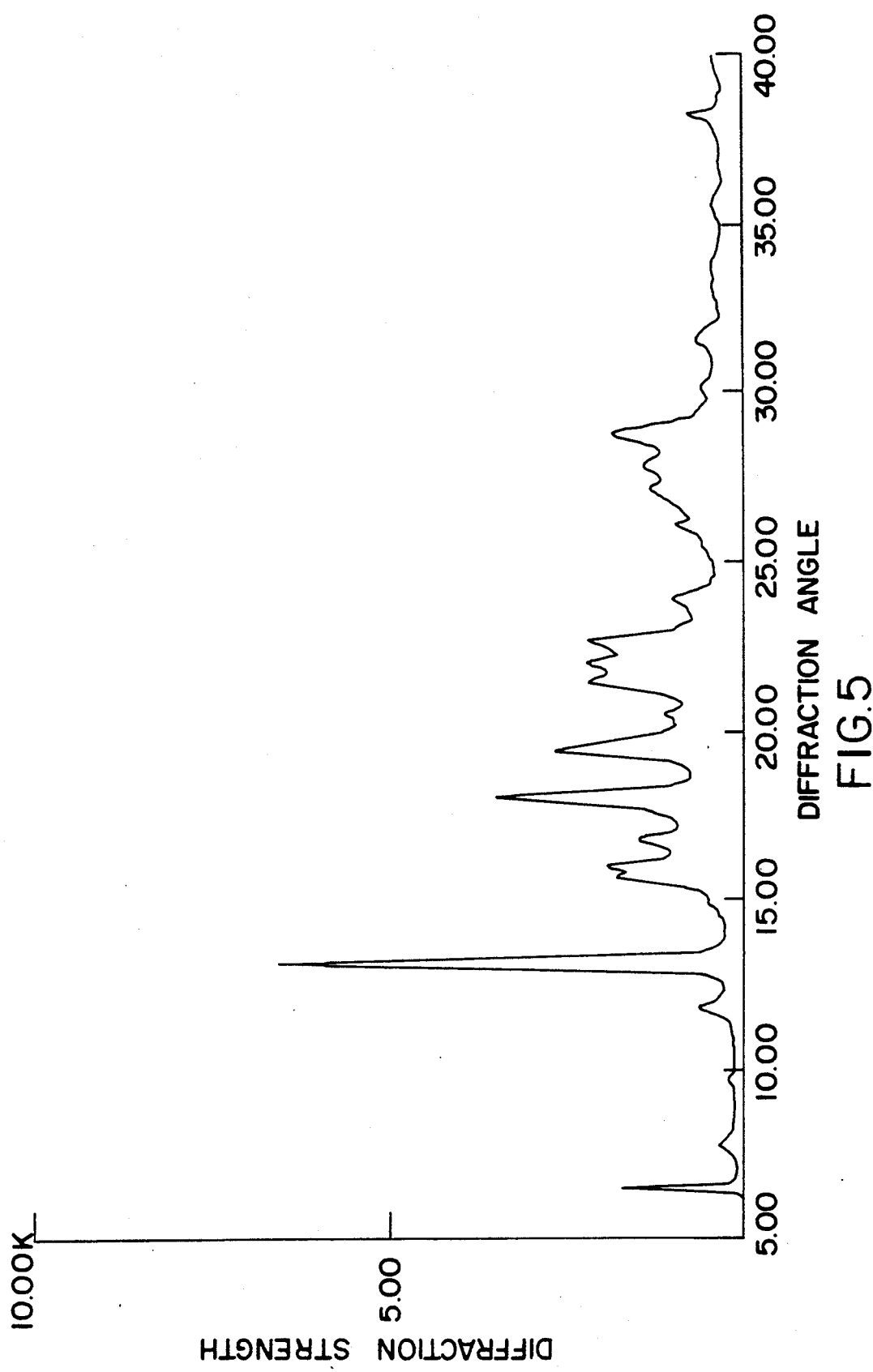

FIG. 5 is a diagram showing the powdery X-ray diffraction of the objective compound synthesized according to the production method of this invention (CuKα, 40 KV, and 40 mA).

FIG. 6 is a diagram showing the powdery X-ray diffraction of the target compound synthesized by the production method of the prior art (CuKα, 40 KV, and 40 mA).

From FIGS. 5 and 6, it is found that the target compounds obtained by the different synthesis methods have respective distinct crystal forms.

This invention will be further illustrated by the following examples, which are not to be considered as limiting the scope of the invention.

EXAMPLES

Example 1.1

2,5-dichloro-2,5-dimethylhexane

First, 48 g (0.328 mole) of 2,5-dimethyl-2,5-hexanediol was suspended in 480 ml of concentrated hydrochloric acid, and the suspension was vigorously stirred at room temperature for 1 hour. After removal of the precipitated crystals by filtration, these crystals were dissolved in 120 ml of $CH_2Cl_2$. This solution was washed with water, dried over $MgSO_4$, and then evaporated to dryness, resulting in 49.3 g (82%) of the aforementioned compound. m.p. 65°–66° C.

NMR δ ($CDCl_3$): 1.63 (12H, s, $CH_3 \times 4$), and 1.97 (4H, s, $CH_2 \times 2$).

1,2,3,4-tetrahydro-1,1,4,4-tetramethyl-6-acetaminonaphthalene

First, 20.28 g (0.15 mole) of acetanilide was suspended in 170 ml of $CH_2Cl_2$. To this suspension, 42 g (0.15 × 2.0 mole) of $AlCl_3$ and 48.07 g (0.15 × 1.75 mole) of 2,5-dichloro-2,5-dimethylhexane were added in this order at −15° C., and the mixture was stirred at the same temperature for 2 hours. The reaction mixture was then poured into 700 ml of ice water. After removal of $CH_2Cl_2$ layer, the aqueous layer was extracted with 100 ml of $CH_2Cl_2$, then the resulting $CH_2Cl_2$ layer was mixed with the aforementioned $CH_2Cl_2$ layer. The combined solution was washed with water, dried over $MgSO_4$, and then evaporated to dryness, resulting in 61.4 g of the residue. To this residue, 110 ml of n-hexane was added, and the solution was allowed to stand overnight in a refrigerator. Then, 29 g (78%) of the precipitated crystals were recrystallized from a mixture of ethanol and water, resulting in 25 g (67%) of the aforementioned compound having a melting point of 116° to 118° C.

NMR δ ($CDCl_3$): 1.27 (12H, s, $CH_3 \times 4$), 1.68 (4H, s, $CH_2 \times 2$), 2.13 (3H, s, $COCH_3$), 7.15–7.45 (3H, m, aromatic H); and 7.69 (1H, broad-s, NH).

Examples 1.2 to 1.14

The same reactions as described in Example 1.1 were conducted under different reaction conditions, and the results shown in Table 3 were obtained as Examples 1.2 to 1.14.

TABLE 3

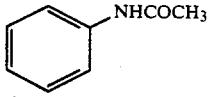

| No. | Starting material (mmol) (I) | Starting material (mmol) (II) | Solvent | Temperature (°C.) | Reaction time (hour) | Catalysis (mmol) AlCl₃ | Product (%) (III) | The recovery of the starting material (%) (I) |
| --- | --- | --- | --- | --- | --- | --- | --- | --- |
| 1-2 | 1.0 | 1.0 | CS₂ | 3 | 1.0 | 2.0 | 70 | 25 |
| 1-3 | 1.0 | 0.5 | CS₂ | 3 | 1.0 | 2.0 | 73 | 8 |
| 1-4 | 1.0 | 1.0 | C₂H₄Cl₂ | 3 | 1.5 | 2.0 | 57 | 29 |
| 1-5 | 1.0 | 1.0 | C₂H₄Cl₂ | −20 | 1.5 | 2.0 | 72 | 15 |
| 1-6 | 1.0 | 1.5 | C₂H₄Cl₂ | −20 | 1.5 | 2.0 | 86 | 6 |
| 1-7 | 1.0 | 1.5 | C₂H₄Cl₂ | −20 | 18.0 | 2.0 | 59 | 13 |
| 1-8 | 1.0 | 1.75 | C₂H₄Cl₂ | −20 | 4.0 | 2.0 | 92 | 5 |
| 1-9 | 1.0 | 1.75 | CH₂Cl₂ | −15 | 2.0 | 2.0 | 92 | 1 |
| 1-10 | 1.0 | 1.75 | CH₂Cl₂ | −20 | 2.8 | 2.0 | 93 | 2 |
| 1-11 | 1.0 | 2.0 | CH₂Cl₂ | −20 | 2.5 | 2.0 | 93 | 2 |
| 1-12 | 1.0 | 1.75 | CH₂Cl₂ | −50 | 8.0 | 2.0 | 50 | 50 |
| 1-13 | 1.0 | 1.75 | CH₂Cl₂ | −30 | 8.0 | 2.0 | 82 | 17 |
| 1-14 | 1.0 | 1.75 | CHCl₃ | −20 | 3.0 | 2.0 | 81 | 18 |

Example 2

Methyl 4-[(5,6,7,8-tetrahydro-5,5,8,8-tetramethyl-2-naphthyl)carbamoyl]benzoate

First, 125 g (0.51 mole) of 1,2,3,4-tetrahydro-1,1,4,4-tetramethyl-6-acetaminonaphthalene was dissolved in 625 ml of $CH_2Cl_2$. To this solution, 206 ml of dimethylaniline and 116.6 g (0.51×1.1 mole) of phosphorus pentachloride were added in this order at −25° C. under a nitrogen atmosphere, and the mixture was stirred at the same temperature for 1.5 hours. To this reaction mixture was added dropwise 2.06 l of methanol, after which the cooling bath was removed and the stirring of the mixture was continued for 2 hours (at −25° C. to room temperature). Furthermore, this reaction mixture was cooled to −25° C., and 306 ml of dimethylaniline and 101.1 g (1.01×0.51 mole) of terephthalic chloride were added thereto in this order. The mixture was stirred at −20° C. to −30° C. for 1 hour. After the reaction was completed, the reaction mixture was poured into 2.6 l of chilled 1N hydrochloric acid, and the mixture was extracted with 1.3 l of $CH_2Cl_2$. The $CH_2Cl_2$ layer was washed with 2.6 l of 1N hydrochloric acid, 4 l of water, 5% aqueous solution of sodium bicarbonate and 4 l of water in this order. After drying over $MgSO_4$, the solution was evaporated to dryness. To this residue was added 740 ml methanol, and the mixture was allowed to stand overnight, resulting in 151 g (81%) of the above-described compound.

NMR (CDCl₃) δ: 1.29 (6H, s, CH₃×2); 1.31 (6H, s, CH₃×2); 1.72 (4H, s, CH₂×2); 3.95 (3H, s, COCH₃); 7.29 (1H, d, H=8 Hz, aromatic H); 7.46 (1H, d-d, J=2 and 8 Hz, aromatic H); 7.64 (1H, d, J=2 Hz, aromatic H); 8.00 (2H, d, J=8 Hz, aromatic H); and 8.13 (2H, d, J=8 Hz, aromatic H).

Example 3

4-[(5,6,7,8-tetrahydro-5,5,8,8-tetramethyl-2-naphthyl)-carbamoyl]benzoic acid

First, 40 g (0.1094 mole) of methyl 4-[(5,6,7,8-tetrahydro-5,5,8,8tetramethyl-2-naphthyl)carbamoyl]benzoate was suspended in 400 ml of methanol. To this suspension was added a solution of 13.1 g (0.1094×3 mole) of sodium hydroxide in 200 ml of water, and the mixture was stirred for 1 hour under reflux by boiling. The reaction mixture was cooled with water, and the pH was adjusted by addition of 2N hydrochloric acid, whereby crystals of the objective compound were precipitated. These crystals were recrystallized from a 1:1 mixture of methanol and water to yield 35.4 g (92%) of the objective compound in pure form.

IR (Nujol) cm⁻¹: 3300, 1700, 1645, 1610, 1270, 535.
NMR(d₆DMSO) δ: 1.24 (12H, s, CH₃×4); 1.67 (4H, s, CH₂×2); 7.30 (1H, d, J=Hz, aromatic H); 8.08 (4H, s, aromatic H); and 10.27 (1H, s).

We claim:

1. A method for preparing a benzoic acid derivative of the general formula (V):

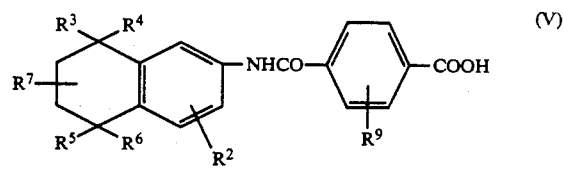

wherein R², R⁷ and R⁹ are independently hydrogen or lower alkyl, and R³, R⁴, R⁵ and R⁶ are independently lower alkyl, which comprises:
(a) subjecting acyl aniline derivative of the general formula (I):

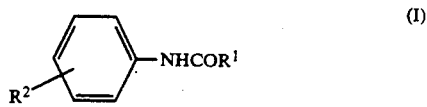

wherein R¹ is lower alkyl or aryl and R² is the same as above, and 1,4-butyl dihalide derivative (II):

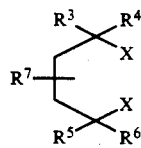

wherein $R^3$, $R^4$, $R^5$, $R^6$, and $R^7$ are respectively the same as above, and X is halogen, to Friedel-Crafts reaction to give a bicyclic amide compound of the general formula (III):

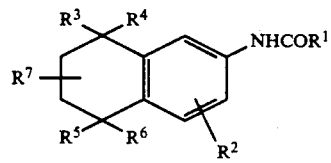

wherein $R^1$, $R^2$, $R^3$, $R^4$, $R^5$, $R^6$, and $R^7$ are respectively the same as above:

(b) reacting the compound (III) obtained in the step (a) with a monoester terephthalic halide to form a compound of the general formula (IV):

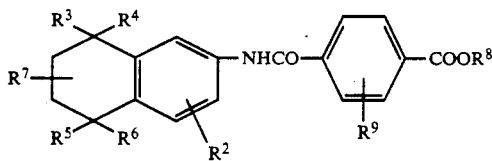

wherein $R^2$, $R^3$, $R^4$, $R^5$, $R^6$, $R^7$, and $R^9$ are respectively the same as above, and $R^8$ is lower alkyl; and (c) subjecting the compound (IV) obtained in the step (b) to de-esterification reaction to give the compound of the general formula (V).

2. A bicyclic amide compound of the general formula (III):

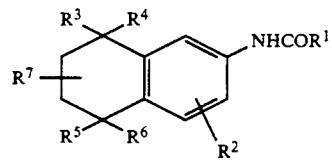

wherein $R^1$ is lower alkyl or aryl, $R^2$ and $R^7$ are independently hydrogen or lower alkyl, and $R^3$, $R^4$, $R^5$ and $R^6$ are independently lower alkyl.

3. A crystal form of 4-[(5,6,7,8-tetrahydro-5,5,8,8-tetramethyl-2-naphthyl)carbamoyl]benzoic acid which exhibits the angles and strength ratios of X-ray diffraction shown in the table below:

| 2 θ | Intensity ratio | 2 θ | Intensity ratio |
| --- | --- | --- | --- |
| 6.58 | 2685 | 23.94 | 677 |
| 7.84 | 455 | 26.14 | 335 |
| 9.80 | 177 | 26.84 | 248 |
| 11.90 | 664 | 26.96 | 310 |
| 13.24 | 10000 | 27.16 | 469 |
| 15.74 | 1558 | 27.8 | 448 |
| 16.02 | 1671 | 28.34 | 332 |
| 16.80 | 871 | 28.76 | 1552 |
| 17.52 | 213 | 29.18 | 202 |
| 17.76 | 1069 | 30.2 | 192 |
| 18.1 | 4112 | 31.66 | 429 |
| 19.5 | 2685 | 31.82 | 213 |
| 19.86 | 924 | 33.96 | 166 |
| 20.56 | 256 | 35.56 | 227 |
| 21.54 | 1385 | 35.78 | 158 |
| 22.08 | 1326 | 38.04 | 237 |
| 22.48 | 987 | 38.28 | 771 |

4. A method for preparing a crystalline 4-[(5,6,7,8-tetrahydro-5,5,8,8-tetramethyl-2-naphthyl)carbamoyl]-benzoic acid claimed in claim 3 comprising the step of recrystallizing a compound of the formula:

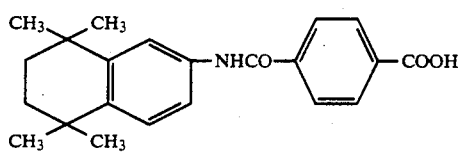

from a methanol type solvent.

* * * * *